United States Patent
Bormashenko

(10) Patent No.: US 9,387,446 B2
(45) Date of Patent: Jul. 12, 2016

(54) EMULSIONS AND METHODS OF MAKING EMULSIONS

(71) Applicant: Ariel-University Research and Development Company Ltd., Ariel (IL)

(72) Inventor: Edward Bormashenko, Ariel (IL)

(73) Assignee: Ariel-University Research and Development Company Ltd., Ariel (IL)

( * ) Notice: Subject to any disclaimer, the term of this patent is extended or adjusted under 35 U.S.C. 154(b) by 0 days.

(21) Appl. No.: 14/345,386

(22) PCT Filed: Sep. 20, 2012

(86) PCT No.: PCT/IB2012/055004
§ 371 (c)(1),
(2) Date: Mar. 17, 2014

(87) PCT Pub. No.: WO2013/042069
PCT Pub. Date: Mar. 28, 2013

(65) Prior Publication Data
US 2014/0350168 A1    Nov. 27, 2014

Related U.S. Application Data

(60) Provisional application No. 61/537,799, filed on Sep. 22, 2011.

(51) Int. Cl.
| | |
|---|---|
| *B01F 3/08* | (2006.01) |
| *A61K 9/107* | (2006.01) |
| *A61K 9/00* | (2006.01) |
| *A61K 47/10* | (2006.01) |
| *A61K 47/44* | (2006.01) |
| *B01F 17/00* | (2006.01) |

(52) U.S. Cl.
CPC ............ *B01F 3/0811* (2013.01); *A61K 9/0014* (2013.01); *A61K 9/107* (2013.01); *A61K 47/10* (2013.01); *A61K 47/44* (2013.01); *B01F 17/0007* (2013.01); *B01F 17/0014* (2013.01); *B01F 17/0021* (2013.01); *B01F 17/0035* (2013.01); *B01F 17/0078* (2013.01); *B01F 2003/0846* (2013.01)

(58) Field of Classification Search
CPC .............. B01F 3/0811; B01F 17/0014; B01F 17/0035; B01F 17/0078; B01F 17/0007; B01F 2003/0846
See application file for complete search history.

(56) References Cited

U.S. PATENT DOCUMENTS

| | | | |
|---|---|---|---|
| 6,290,941 B1 * | 9/2001 | Lahanas et al. | 424/69 |
| 6,391,321 B1 | 5/2002 | Gers-Barlag et al. | |
| 2003/0047688 A1 * | 3/2003 | Faris et al. | 250/432 R |
| 2008/0249194 A1 * | 10/2008 | Tanguy et al. | 516/38 |

FOREIGN PATENT DOCUMENTS

DE    102007041485 A1 *    3/2009

OTHER PUBLICATIONS

EPO machine translation of DE 102007041485 A1, May 2015.*
Melle et al. "Pickering Emulsions with Controllable Stability", Langmuir, 2005, 21, 2158-2162.*

(Continued)

*Primary Examiner* — Nicole M Buie-Hatcher

(57) ABSTRACT

Disclosed are methods for making emulsions and emulsions, that in some embodiments can be considered to be Pickering emulsions.

10 Claims, 2 Drawing Sheets

(56) References Cited

OTHER PUBLICATIONS

Antonucci et al., A Comparative Analysis of Structural and Surface Effects in the Electrochemical Corrosion of Carbons. Mater. Chem. Phys. 1989;21:495-506.
Aussillous and Quéré, Liquid marbles. Nature. Jun. 21, 2001;411(6840):924-927.
Aussillous and Quéré, Properties of liquid marbles. Proc R Soc. A 2006;462:973-999.
Bhosale et al., Mechanically robust nanoparticle stabilized transparent liquid marbles. Appl. Phys. Lett. 2008;93:034109 (3pp).
Bhosale and Panchagnula, On Synthesizing Solid Polyelectrolyte Microspheres from Evaporating Liquid Marbles. Langmuir. Jul. 6, 2010;26(13):10745-10749.
Bormashenko and Musin, Revealing of water surface pollution with liquid marbles. Appl Surf Science 2009;255:6429-6431.
Bormashenko et al., "Petal Effect" on Surfaces Based on Lycopodium: High-Stick Surfaces Demonstrating High Apparent Contact Angles. J. Phys. Chem. C 2009;113:5568-5572.
Bormashenko et al., Interfacial and conductive properties of liquid marbles coated with carbon black. Powder Technology 2010;203:529-533.
Bormashenko et al., Janus Droplets: Liquid Marbles Coated with Dielectric/Semiconductor Particles. Langmuir. Jan. 4, 2011;27(1):7-10.
Bormashenko et al., Micropump based on liquid marbles. Applied Physics Letters, 2010;97:091908.
Bormashenko et al., New Investigations on Ferrofluidics: Ferrofluidic Marbles and Magnetic-Field-Driven Drops on Superhydrophobic Surfaces. Langmuir. Nov. 4, 2008;24(21):12119-12122.
Bormashenko et al., On the Mechanism of Floating and Sliding of Liquid Marbles. Chemphyschem. Mar. 9, 2009;10(4):654-656.
Bormashenko et al., On the Nature of the Friction between Nonstick Droplets and Solid Substrates. Langmuir. Aug. 3, 2010;26(15):12479-12482.
Bormashenko et al., Shape, Vibrations, and Effective Surface Tension of Water Marbles. Langmuir. Feb. 17, 2009;25(4):1893-1896.
Bormashenko et al., Surface tension of liquid marbles. Colloids and Surfaces A 2009;351:78-82.
Bormashenko et al., Water rolling and floating upon water: Marbles supported by a water/marble interface. J Colloid Interface Sci. May 1, 2009;333(1):419-421.
Bormashenko et al., Wetting Properties of the Multiscaled Nanostructured Polymer and Metallic Superhydrophobic Surfaces. Langmuir. Nov. 21, 2006;22(24):9982-9985.
Bormashenko, Liquid marbles: Properties and applications. Curr Opin Colloid Interface Sci. 2011;16:266-271.
Bormashenko, Stable water and glycerol marbles immersed in organic liquids: From liquid marbles to Pickering-like emulsions. J Colloid Interface Sci. Jan. 15, 2012;366(1):196-199.
International Search Report and Written Opinion issued in PCT/IB2012/055004 dated Feb. 28, 2013.
Dandan and Erbil, Evaporation Rate of Graphite Liquid Marbles: Comparison with Water Droplets. Langmuir. Jul. 21, 2009;25(14):8362-8367.
Dupin et al., Stimulus-responsive liquid marbles. J Am Chem Soc. Apr. 22, 2009;131(15):5386-5387.
Eshtiaghi et al., Liquid marble formation: Spreading coefficients or kinetic energy? Powder Technology 2009;196:126-132.
Forny et al., Storing water in powder form by self-assembling hydrophobic silica nanoparticles. Powder Technology, 2007;171:15-24.
Fujii et al., pH-responsive liquid marbles stabilized with poly(2-vinylpyridine) particles. Soft Matter 2010;6:635-640.
Fujii and Murakami, Smart Particles as Foam and Liquid Stabilizer. KONA Powder and Particle J. 2008;26:153-166.
Gao and McCarthy, Ionic Liquid Marbles. Langmuir. Oct. 9, 2007;23(21):10445-10447.
Kim et al., Janus Microspheres for a Highly Flexible and Impregnable Water-Repelling Interface. Angew Chem Int Ed Engl. Mar. 29, 2010;49(14):2535-2538.
Mahadevan, Non-stick water. Nature. Jun. 21, 2001;411(6840):895-896.
Matsukuma et al., Preparation of Low-Surface-Energy Poly[2-(perfluorooctypethyl acrylate] Microparticles and Its Application to Liquid Marble Formation. Langmuir. Feb. 15, 2011;27(4):1269-1274.
McEleney et al., Liquid marble formation using hydrophobic powders. Chemical Engineering Journal 2009;147:373-382.
McHale and Newton, Liquid Marbles: Principles and Applications. Soft Matter Mar. 2011;7(12):5473-5481.
McHale et al., Electrowetting of Nonwetting Liquids and Liquid Marbles. Langmuir. Jan. 16, 2007;23(2):918-924.
Newton et al., Electrowetting of liquid marbles, J. Phys. D: Appl. Phys. 2007;40:20-24.
Nguyen et al., Observation of the liquid marble morphology using confocal microscopy. Chemical Engineering Journal 2010;162:396-405.
Pickering, CXCVI.—Emulsions. Chem Soc, Trans. 1907;91:2001-2021.
Tian et al., Liquid marble for gas sensing. Chem Commun (Camb). Jul. 14, 2010;46(26):4734-4736.
Tosun and Erbil, Evaporation rate of PTFE liquid marbles. Applied Surface Sci., 2009;256:1278-1283.
Xue et al., Magnetic Liquid Marbles: A "Precise" Miniature Reactor. Adv Mater. Nov. 16, 2010;22(43):4814-4818.
Zhao et al., Magnetic Liquid Marbles: Manipulation of Liquid Droplets Using Highly Hydrophobic Fe3O4 Nanoparticles. Adv Mater. Feb. 9, 2010;22(6):707-710.

\* cited by examiner

EMULSIONS AND METHODS OF MAKING EMULSIONS

RELATED APPLICATION

The present invention is filed under 35 U.S.C. §371 as the U.S. national phase of International Application No. PCT/IB2012/055004, filed 20 Sep. 2012, which designated the U.S. and claims priority to U.S. Provisional Patent Application No. 61/537,799 filed 22 Sep. 2011, which is hereby incorporated in its entirety including all tables, figures, and claims.

FIELD AND BACKGROUND OF THE INVENTION

The invention, in some embodiments, relates to the field of emulsions.

An emulsion is a mixture of at least two normally-immiscible liquids. In an emulsion, at least one liquid, constituting the dispersed phase, is present as a plurality of discrete droplets dispersed in at least one second liquid, constituting the continuous phase.

Typically, emulsifiers are added to an emulsion. Emulsifiers are materials that are soluble in one of the liquids of the emulsion to promote formation and stability of an emulsion. The nature of a specific emulsifier or combination of emulsifiers also assists in determining whether a given mixture will be a water-in-oil (aqueous dispersed phase) or oil-in-water emulsion (non-aqueous dispersed phase).

One specific type of emulsion is the Pickering emulsion. In a Pickering emulsion, the emulsion includes a shell of solid particles located at the interfaces between the dispersed phase droplets and the continuous phase. Pickering emulsions are typically made by combining an oil, a water and solid particles (typically less than 100 micrometers in diameter) and then vigorously mixing, for example in a blender. Depending on the relative amounts of the water and oil, the size of the solid particles and the nature of the solid particles (generally the phase that preferentially wets the particle will be the continuous phase), a water-in-oil or oil-in-water Pickering emulsion is formed, where the presence of the solid particles increases stability of the emulsion by preventing the dispersed phase droplets from coalescing.

SUMMARY OF THE INVENTION

The invention, in some embodiments, relates to methods for making emulsions having a dispersed phase comprising liquid marbles, substantially Pickering emulsions. The invention, in some embodiments, relates to emulsions having a dispersed phase comprising liquid marbles.

Some aspects of the invention have been published as a scientific article in the Journal of Colloid and Interface Science 2012, 366, pp. 196-199 available online on Sep. 24, 2011, which is included by reference as if fully set-forth herein.

According to an aspect of some embodiments of the invention, there is provided a method of making an emulsion having a dispersed phase in a continuous phase, the method comprising:
  a. providing a first liquid intended as the continuous phase of the emulsion;
  b. providing a plurality of liquid marbles intended as components of the dispersed phase of the emulsion, the liquid marbles comprising a droplet of a second liquid covered with a shell of particles;
  c. subsequent to b, immersing the plurality of liquid marbles in the first liquid,
thereby making the emulsion wherein the immersed plurality of liquid marbles comprising a droplet of the second liquid constitute at least a portion of the dispersed phase of the emulsion and the first liquid constitutes the continuous phase of the emulsion.

In some embodiments, the providing a plurality of liquid marbles comprises:
making the liquid marbles by,
  placing the particles on a surface;
  setting droplets of the second liquid on the surface; and
  allowing the set droplets to roll on the surface so as to be covered by the particles to form the shell of particles, thereby providing the liquid marbles.

In some embodiments, the providing of the plurality of liquid marbles comprises:
  making liquid marbles comprising a droplet of the second liquid covered with the shell of the particles;
  prior to the immersing of the plurality of liquid marbles in the first liquid, selecting only a portion of the made liquid marbles for the immersion;
  immersing the selected made liquid marbles in the first liquid; and
  not immersing the not-selected made liquid marbles in the first liquid.

In some embodiments, the method further comprises:
  d. providing a plurality of liquid marbles intended as a component of the dispersed phase of the emulsion in addition to the plurality of liquid marbles comprising a droplet of second liquid, each such liquid marble comprising a droplet of a third liquid covered with a shell of particles; and
  e. subsequent to d, immersing the plurality of liquid marbles comprising a droplet of the third liquid in the first liquid,
thereby making the emulsion wherein:
  the immersed plurality of liquid marbles comprising a droplet of the second liquid constitutes a portion of the dispersed phase of the emulsion;
  the immersed plurality of liquid marbles comprising a droplet of the third liquid constitutes a portion of the dispersed phase of the emulsion; and
  the first liquid constitutes the continuous phase of the emulsion.

According to an aspect of some embodiments of the invention, there is also provided an emulsion, comprising:
  a continuous phase of a first liquid; and
  a dispersed phase comprising a plurality of liquid marbles, the liquid marbles
  comprising a droplet of a liquid covered with a shell of particles,
wherein at least one of:
  the first liquid constituting the continuous phase includes a non-soluble constituent suspended therein;
  a size distribution of the dispersed phase is a non-probability distribution;
  the dispersed phase includes at least two distinct populations of the liquid marbles;
  the dispersed phase includes at least one distinct population of liquid marbles which droplet of liquid is miscible with the first liquid of the continuous phase;
  the dispersed phase includes at least one distinct population of liquid marbles which droplet of liquid is substantially different from and miscible with the first liquid of the continuous phase;

the dispersed phase includes at least one distinct population of liquid marbles which droplet of liquid comprises a non-soluble constituent suspended therein;

the dispersed phase includes at least one distinct population of liquid marbles having an average diameter of not less than 100 micrometers;

the dispersed phase includes at least one distinct population of liquid marbles which shell of particles is a mixture of at least two different materials;

the dispersed phase includes at least one distinct population of liquid marbles which shell of particles has an average dimension of not less than 10 micrometers; and the emulsion comprises at least two components that tend to chemically react when in contact under normal conditions, the at least two components mutually isolated from such contact by virtue of isolation of at least one of the components in a liquid marble.

According to an aspect of some embodiments of the invention, there is also provided an emulsion comprising:

a continuous phase including at least one oil; and a dispersed phase including liquid marbles, the liquid marbles comprising:

droplets of a liquid selected from the group consisting of water, water solutions, glycerol, and glycerol solutions; and covering the surface of the droplets, a shell of particles substantially insoluble in the continuous phase and in the droplets of liquid.

According to an aspect of some embodiments of the invention, there is also provided a method of making an emulsion comprising:

a) providing a liquid including at least one oil;

b) providing a liquid marble of a droplet of a liquid selected from the group consisting of water, water solutions, glycerol and glycerol solutions which surface is covered with a shell of particles substantially insoluble in the droplet of liquid and in the liquid including at least one oil;

c) subsequent to b, immersing the liquid marble in the liquid including at least one oil thereby making the emulsion wherein the liquid marble constitutes a dispersed phase and the liquid including at least one oil constitutes a continuous phase.

Unless otherwise defined, all technical and scientific terms used herein have the same meaning as commonly understood by one of ordinary skill in the art to which the invention pertains. In case of conflict, the specification, including definitions, will take precedence.

As used herein, the terms "comprising", "including", "having" and grammatical variants thereof are to be taken as specifying the stated features, integers, steps or components but do not preclude the addition of one or more additional features, integers, steps, components or groups thereof. These terms encompass the terms "consisting of" and "consisting essentially of".

As used herein, the indefinite articles "a" and "an" mean "at least one" or "one or more" unless the context clearly dictates otherwise.

As used herein, when a numerical value is preceded by the term "about" the term "about" is intended to indicate +/−10%.

BRIEF DESCRIPTION OF THE FIGURES

Some embodiments of the invention are described herein with reference to the accompanying figure. The description, together with the figure, makes apparent to a person having ordinary skill in the art how some embodiments of the invention may be practiced. The figure is for the purpose of illustrative discussion and no attempt is made to show structural details of an embodiment in more detail than is necessary for a fundamental understanding of the invention. For the sake of clarity, some objects depicted in the figure are not to scale.

In the Figures.

DESCRIPTION OF SOME EMBODIMENTS OF THE INVENTION

Figure 1:
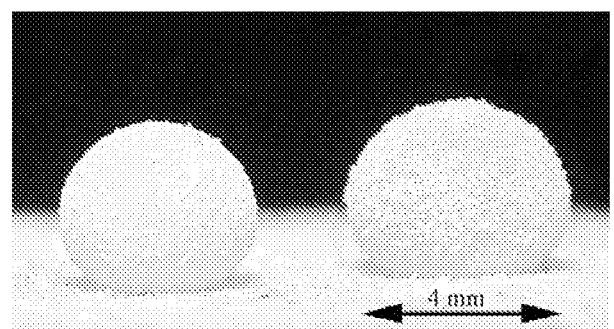
FIG. 1 is a reproduction of a photograph of liquid marbles comprising a droplet of water, (left side, with a shell of PVDF particles; right side, with a shell of lycopodium powder particles) resting on a superhydrophobic surface.

The invention, in some embodiments, relates to methods for making emulsions having a dispersed phase comprising liquid marbles, substantially Pickering emulsions. The invention, in some embodiments, relates to emulsions having a dispersed phase comprising liquid marbles.

As known in the art, in a Pickering emulsion solid particles are located in the interfaces between the dispersed phase droplets and the continuous phase [36]. Apparently, the presence of the solid particles increases stability of the emulsion by preventing the dispersed phase droplets from coalescing.

Liquid marbles [1-35, 37-40] comprise a droplet of water or the like (e.g., water solutions, glycerol, glycerol solutions, ionic liquids [8]), the outer surface of which is completely covered by a shell of solid particles (hydrophobic or hydrophilic particles). When such a liquid marble rests on a solid or liquid surface, the marble and surface are separated by gas (e.g., air or vapor) trapped in the rough surface of the particles of the shell forming a gas layer similarly to a Leidenfrost droplet [1, 2, 20]. As a result of this gas layer interface, liquid marbles exhibit extremely low friction [1, 2, 39]. The practical use of marbles is limited by the fact that the shell is gas-permeable so that the liquid making up the core evaporates at ambient conditions. [11, 35]

Herein are disclosed methods of making emulsions having a dispersed phase comprising liquid marbles. In some embodiments, such emulsions can be considered as a type of Pickering emulsion due to the presence of a dispersed phase including a shell of solid particles. In some embodiments, the emulsions are devoid of an emulsifier. Typically, an emulsion according to the teachings herein comprises a large plurality of liquid marbles, e.g., not less than 5, not less than 10, not less than 100 and even not less than 1000 marbles.

Method of Making an Emulsion

According to an aspect of some embodiments of the teachings herein, there is provided a method of making an emulsion comprising:

a. providing a first liquid intended as the continuous phase of the emulsion;

b. providing a plurality of liquid marbles intended as components of the dispersed phase of the emulsion, said liquid marbles comprising a droplet of a second liquid covered with a shell of particles;

c. subsequent to b, immersing said plurality of liquid marbles in said first liquid, thereby making the emulsion wherein said immersed plurality of liquid marbles comprising a droplet of said second liquid constitute at least a portion of the dispersed phase of the emulsion and said first liquid constitutes the continuous phase of the emulsion.

As is clear to a person having ordinary skill in the art upon perusal of the description herein, the teachings herein allow making emulsions having specific selected rheological and other desirable properties, with the use of few or no additives such as emulsifiers and/or surfactants and/or cosolvents.

Thus according to an aspect of some embodiments of the teachings therein, there is also provided an emulsion comprising a continuous phase of a first liquid; and a dispersed phase comprising a plurality liquid marbles, the liquid marbles comprising a droplet of a liquid covered with a shell of particles.

Providing Liquid Marbles

The liquid marbles can be provided in any suitable way. In some embodiments, the liquid marbled are made, using any suitable method e.g., methods known in the art. For example, in some embodiments, the liquid marbles are made by: forming a droplet of the second liquid; and coating the surface of the droplet with the particles, thereby forming the shell of particles. In some such embodiments, a liquid marble is made by: providing a layer of the particles on a surface; depositing a droplet of the second liquid on the layer of particles (e.g., using a pipette, for example, a metered pipette); and moving the droplet of the second liquid on the layer of particles (e.g., by tilting the surface, applying a fluid flow such as a gas flow to roll the particles on the layer of particles and/or the surface is tilted when the droplet is applied) so as to coat the surface of the droplet with the particles, thereby forming the liquid marble.

Thus, in some embodiments, the providing of the plurality of the liquid marbles comprises:

making the liquid marbles by:
　　placing the particles on a surface;
　　setting droplets of the second liquid on the surface; and
　　allowing the set droplets to roll on the surface so as to be covered by the particles to form the shell of particles, thereby providing the liquid marbles.

Placing Particles

The particles are placed on the surface in any suitable fashion, for example by spreading, dropping, sowing or otherwise dispensing the particles on the surface. In some embodiments, the particles are placed on the surface, a batch of marbles is formed, and when necessary, more particles are placed to replenish the amount of particles on the surface. In some embodiments, the placing of the particles on the surface is substantially continuous or intermittent.

Rolling

Rolling of the droplets is achieved in any suitable way. In some embodiments, the surface is sloped: the droplets are set on the surface and roll down the surface as a result of the slope. In some embodiments, the slope is fixed. In some embodiments, the surface is tiltable allowing the degree and direction of the slope to be changed.

Complete Layer of Particles

In some embodiments, the particles are placed on the surface to form a complete layer so that the underlying surface is not apparent. In some such embodiments, the nature of the underlying surface is of relative little significance and can be any suitable surface, typically smooth so that the layer of particles placed thereupon is uniformly smooth. In such embodiments, droplets of liquid roll on a layer of particles.

Some such embodiments have a number of disadvantages, including: the resistance to rolling, especially for small droplets of liquid, may be too great; generating and maintaining the layer of particles to be suitable for rolling of droplets may be challenging; a rolling droplet may cause furrows or dips to form in the layer of particle, so the droplet, or succeeding droplets, may not successfully roll.

Sparse Layer of Particles

In some embodiments, the particles are placed on the surface sparsely, that is to say, that at least some of the surface is apparent through the layer of particles thereupon. In such embodiments, the surface can be any suitable surface and is typically smooth so that the droplets roll easily on the surface. In such embodiments, a rolling droplet contacts both particles and the surface. In some such embodiments, to assist in ensuring rolling, avoid spreading of the droplet on the surface or adhesion of the droplet to the surface that potentially slows the rolling, the surface has a low wettability by the second liquid that makes up the droplets.

Wettability of the Surface

In some embodiments, the surface has a low wettability by the second liquid.

If a droplet of the second liquid contacts a portion of a surface having a low wettability by the second liquid, the droplet does not spread or adhere to the surface but rolls along the surface. Low wettability helps ensure that the droplets roll quickly and do not collide to coalesce. Importantly, such low wettability allows the layer of particles to be as sparse as desired to assist in ensuring that the droplets can easily and quickly roll on the surface.

The degree of wettability of a surface of a material by a liquid is typical expressed by the contact angle at a material/liquid interface. A material having a contact angle of less than or equal to 90° is considered wettable while a contact angle of greater than 90° is considered of low wettability. When the contact angle of water to a surface is greater than 90° the surface is considered hydrophobic, and when the contact angle of water to a surface is greater than 140° the surface is considered superhydrophobic. When the contact angle of a water-immiscible liquid to a surface is greater than 90° the surface is considered oleophobic to that liquid, and when the contact angle of the water immiscible liquid to a surface is greater than 140° the surface is considered superoleophobic to that liquid.

It is generally accepted that there are two types of contact angles: Young equilibrium contact angle and apparent contact angle.

The Young equilibrium contact angle can be established for any material for which a flat, smooth, non-deformable, homogeneous chemically non-active surface can be fashioned. Specifically, a drop of liquid is placed on such a surface and the Young contact angle measured, for example using a goniometer.

For powders, chemically heterogeneous surfaces, or rough (i.e., having nanoscale or larger features, in some cases leading to the Lotus effect) surfaces, the Young contact angle cannot be measured, and instead, the apparent contact angle is measured. The apparent contact angle is defined as the angle between the tangent to the liquid-film interface and the apparent solid surface as macroscopically observed. For powders, apparent contact angle is often measured by placing a drop of liquid on a flat adhesive surface (e.g., sticky tape) covered with the powder (see Marmur A "A guide to the equilibrium contact angles maze" in Contact Angle Wettability and Adhesion, V. 6, pp. 3-18, ed. by K. L. Mittal, VSP, Leiden, 2009).

It has been found that in some embodiments, the less the wettability of the surface by the second liquid, the more satisfactory the process of covering the droplets of the second liquid with a shell of particles.

Accordingly, in some embodiments, the second liquid has a contact angle (Young equilibrium contact angle or apparent contact angle, whichever relevant) of not less than 100° not less than 110°, not less than 120° and even not less than 130° with the surface. In such embodiments, if the second liquid is water-miscible the surface is hydrophobic and if the second liquid is water-immiscible the surface is oleophobic.

In some embodiments, the second liquid has a contact angle (Young equilibrium contact angle or apparent contact angle, whichever relevant) of not less than 140°, not less than 150° and even not less than 160° with the surface. In such embodiments, if the second liquid is water-miscible the surface is superhydrophobic and if the second liquid is water-immiscible the surface is superoleophobic.

Setting of the Droplets

The droplets of the second liquid are set on the surface and/or on top of the layer of particles in any suitable fashion.

In some embodiments, the setting of the droplets comprises:
generating droplets of the second liquid; and
placing the generated droplets on the surface.

In some embodiments, generated droplets are directed at the surface. In some embodiments, the droplets are allowed to settle on the surface and/or on top of the layer of particles.

The droplets can be generated in any suitable fashion using any suitable component. Depending on the embodiment, suitable components for generating droplets to implement the teachings herein include sprayers (having any suitable spray nozzle), aerosol sprayers, atomizers (including, but not limited to rotary and ultrasonic atomizers), nebulizers, electrosprays, thermosprays, vibrating orifice aerosol generators, pipettes and droppers.

Nature of the Liquids

The first and second liquids are any suitable pair of liquids, typically (though not necessarily) two different liquids.

Mutually Immiscible Liquids

In the art, it is know that emulsions, including Pickering emulsions, comprise two mutually-immiscible liquids, a first liquid that constitutes a continuous phase of the emulsion, and a second liquid that constitutes a dispersed phase of the emulsion. When the continuous phase is miscible with water and the dispersed phase is immiscible with water, the emulsion is an oil-in water emulsion. When the continuous phase is immiscible with water and the dispersed phase is miscible with water, the emulsion is a water-in-oil emulsion.

Similarly, in some embodiments, the first liquid and the second liquid are mutually immiscible. In some embodiments, one of the first and second liquids is water-miscible and another is water-immiscible. In some embodiments, the first liquid is immiscible in water and the second liquid is miscible in water, so that the emulsion is a water-in-oil emulsion. In some embodiments, the first liquid is miscible in water and the second liquid is immiscible in water, so that the emulsion is an oil-in-water emulsion.

Mutually Miscible Liquids

Despite the above, since in the method of making emulsions according to the teachings herein liquid marbles making up the dispersed phase are first provided and only subsequently immersed in the continuous phase, in some embodiments, the first liquid and the second liquid are mutually miscible.

In some embodiments, the first liquid and the second liquid are mutually miscible. In some embodiments, the first liquid and the second liquid are different and mutually miscible. In some embodiments, the first and the second liquid are both water-miscible. In some embodiments, the first and the second liquid are both water-immiscible.

Water-Miscible Liquids

In some embodiments, at least one of the first liquid and the second liquid is a water-miscible liquid. In some embodiments, at least one of the first liquid and the second liquid is a water miscible liquid comprising a single (typically substantially pure) water-miscible material. In some embodiments, at least one of the first liquid and the second liquid is a water miscible liquid comprising a mixture of at least two different materials. In some embodiments, at least one of the first liquid and the second liquid is an acidic water miscible liquid having a pH not greater than 6, not greater than 5 and even not greater than 4. In some embodiments, at least one of the first liquid and the second liquid is a neutral water miscible liquid having a pH between 6 and 8 (inclusive). In some embodiments, at least one of the first liquid and the second liquid is a basic water miscible liquid having a pH not less than 8, not less than 9 and even not less than 10.

In some embodiments, at least one of the first liquid and the second liquid is a water-miscible liquid selected from the group consisting of water, water solutions, glycerol and glycerol solutions.

In some embodiments, at least one of the first liquid and the second liquid is a water-miscible liquid including at least one water-soluble constituent dissolved in the water-miscible liquid. For example, in some such embodiments, a water-soluble constituent is an active pharmaceutical ingredient.

Water-Immiscible Liquids

In some embodiments, an emulsion according to the teachings herein comprises a liquid including at least one oil. As used herein, the term "oil" refers to a liquid that is substantially insoluble and immiscible in water.

In some embodiments, at least one of the first liquid and the second liquid is a water-immiscible liquid comprising at least one oil, in some embodiments, a mixture of at least two oils.

In some embodiments, the water-immiscible liquid comprises at least one material selected from the group consisting of non-polar oils, petroleum ether, toluene, xylene (e.g., ortho-, meta-, para-isomers and mixtures thereof), carbon tetrachloride ($CCl_4$), dichloromethane, 1,2-dichloroethane, chloroform, silicone oils (polyalkyl siloxane (such as cyclomethicone and/or dimethicone), polyaryl siloxane, polyalkylaryl siloxane, polyether siloxane copolymer, and combinations thereof, e.g., polydimethylsiloxane such as Sylgard 184 and Dow Corning 2000), edible oils. vegetable oils (sunflower, rapeseed, olive, peanut, coconut, soy), animal oils and mixtures thereof.

In some embodiments, at least one of the first liquid and the second liquid is a water-immiscible liquid including at least one water-insoluble constituent dissolved in the water-immiscible liquid. For example, in some such embodiments, a water-insoluble constituent is an active pharmaceutical ingredient.

Non-Soluble Constituent

Since in the method of making emulsions according to the teachings herein liquid marbles making up the dispersed phase are first provided and only subsequently immersed in the continuous phase, in some embodiments, the second liquid making up the droplet of a liquid marble comprises a non-soluble constituent suspended therein. For example, in some embodiments, such a non-soluble constituent is a non-soluble solid (e.g., of $TiO_2$) and the second liquid is a water suspension or sol. For example, in some embodiments, such a non-soluble constituent is a non-soluble liquid and the liquid marbles comprise droplets of a suspension or a colloid where covering the surface of the droplets is a shell of the particles.

Accordingly, in some embodiments, the second liquid includes a non-soluble constituent suspended therein. In some such embodiments, the second liquid is selected from the group consisting of a colloid, an emulsion, water-in-oil emulsion, oil-in-water emulsion, a sol (solid dispersed phase in a liquid continuous phase), a hydrocolloid (hydrophilic polymers in water) and a suspension (solid particles dispersed in a liquid continuous phase that do eventually settle)

Droplet Size

The size of the droplets of the second liquid making up the liquid marbles of an emulsion according to the teachings herein is any suitable size.

In some embodiments, the droplets have an average diameter of not less than 50 nm, not less than 75 nm and even not less than 100 nm.

In some embodiments, the droplets have an average diameter of not more than 10 mm, not more than 5 mm, not more than 4 mm, not more than 3 mm, not more than 2 mm and even not more than 1 mm.

In this context, it is important to note that in known Pickering emulsions, the droplets are relatively small, while in some embodiments of the emulsions according to the teachings herein, the droplets are comparatively larger. Specifically, in some embodiments, the droplets have an average diameter of not less than 100 micrometers, not less than 200 micrometers, not less than 500 micrometers and even not less than 1 mm.

Particles Constituting the Shell of the Liquid Marbles

Like in all Pickering emulsions, the shell of particles covering the droplets of the second liquid according to the teachings herein are adsorbed onto the interface between the two phases. It is generally accepted that the shell of particles stabilizes a Pickering emulsion by preventing contact between the liquid in any two droplets, preventing droplet coalescence and eventual phase-separation.

Any suitable particle or mixture of particles can be used in implementing the teachings herein, especially any suitable particle known in the art to be suitable for use in implementing a Pickering emulsion.

In some embodiments, the particles are solid particles. In some embodiments, the particles are substantially insoluble in the first liquid and in the second liquid.

Wettability of Particles

In known Pickering emulsions the particles covering the dispersed phase droplets are preferentially wettable by the liquid of the continuous phase rather than the liquid of the dispersed phase. In known Pickering emulsions, the nature of the solid particles often determines whether the emulsion is a water-in-oil or oil-in-water emulsion. Specifically, hydrophobic particles (not wettable by water) stabilize water-in-oil emulsions, whereas hydrophilic particles (wettable by water) stabilize oil-in-water emulsions.

Accordingly, in some embodiments, the particles are more wettable by the first liquid (intended to be the continuous phase) than by the second liquid (intended to be the dispersed phase). That said, since in the method of making emulsions described herein liquid marbles making up the dispersed phase are first provided and only subsequently immersed in the continuous phase, in some embodiments the particles are more wettable by the second liquid (intended to be the dispersed phase) than by the first liquid (intended to be the continuous phase).

In some embodiments, the second liquid has an apparent contact angle of not less than 100°, not less than 110°, not less than 120° and even not less than 130° with the particles. In such embodiments, if the second liquid is water-miscible the particles are hydrophobic, and if the second liquid is water-immiscible the particles are oleophobic.

In some embodiments, the second liquid has an apparent contact angle of not less than 140°, not less than 150° and even not less than 160° with the particles. In such embodiments, if the second liquid is water-miscible the particles are superhydrophobic, and if the second liquid is water-immiscible the particles are superoleophobic.

Particles Material

In some embodiments, the particles placed on the surface as described above are all of a single material, so that the particles of a shell of a given individual marble are substantially all of a single material.

That said, in some embodiments, particles of at least two different materials are simultaneously placed on the surface as described above, so that the particles of a shell of a given individual marble are a mixture of at least two different materials.

In some embodiments, the particles comprise particles selected from the group consisting of polyethylene (PE), polypropylene (PP), polytetrafluoroethylene (PTFE), silica (colloidal silica, fumed silica), carbon black, adsorbed polyelectrolytes (poly(sodium styrene sulfonate) PSS; polyacrylic acid (PAA); poly[N-(3-aminopropyl)methacrylamide (APMA); polyethyleneamine (PEA); polyvinylidene difluoride (PVDF); polypeptides (e.g., proteins such as casein, poly-arginine, corn protein zein); polysaccharides (e.g., pectin, chitosan, cellulose); lechitins; alginates; carrageenan; latex particles, amphiphilic particles (e.g, Janus particles); particulate biological-material (e.g. from a biological source especially as from a botanical source, e.g., pollen, lycopodium powder, seeds, pulverized leaves, stems, bark, such as of spices and herbs)

Particle Size

Particles of any suitable size or distribution of sizes can be used in implementing the teachings herein, especially any size or distribution of sizes known in the art to be suitable for use in implementing a Pickering emulsion. For example, as known in the art of Pickering emulsions, in some embodiments the particles are nanoparticles.

In some embodiments, the particles have an average dimension (diameter for substantially spherical particles, largest dimension for other shapes) of not less than 20 nm, not less than 30 nm, not less than 40 nm and even not less than 50 nm.

In some embodiments, the particles have an average dimension of not more than 2 mm, not more than 1 mm and even not more than 500 micrometers.

In this context, it is important to note that in known Pickering emulsions, the particles in the shell of particles have an average dimension that is relatively small, while in some embodiments of the emulsions according to the teachings herein, the particles are comparatively larger. In some embodiments, the particles in the shell of particles have an average dimension of not less than 10 micrometers, not less than 20 micrometers and even not less than 50 micrometers.

Dispersed-Phase Size Distribution

As is known to a person having ordinary skill in the art, Pickering emulsions are made by vigorously mixing together a first liquid, a second liquid and particles so that a dispersed phase is formed having a probability distribution of sizes of the dispersed phase particles. Specifically, the dispersed phase is typically found with a Gaussian distribution of droplet sizes determined by thermodynamic factors during the mixing step in the formation of the emulsion, what is herein termed a standard or probability distribution.

Since in the method of making emulsions according to the teachings herein liquid marbles making up the dispersed phase are first provided and only subsequently immersed in the continuous phase, in some embodiments the distribution of sizes of the liquid marbles constituting the dispersed phase particles is a non-probability distribution, allowing selection of rheological properties of the emulsion.

In some embodiments, the dispersed phase of an emulsion as taught herein has a non-probability distribution of liquid marbles. In some embodiments, the dispersed phase of an emulsion as taught herein has a selected distribution of droplet size, that is to say, the distribution is specifically selected when the emulsion is being made.

In some embodiments, the dispersed phase of an emulsion as taught herein has a non-standard narrow distribution of droplet (and thus liquid marble) sizes. In such embodiments, the droplet (and thus liquid marble) size has a very narrow Gaussian-like distribution, that is to say a distribution of droplet (and thus liquid marble) size determined by non-thermodynamic factors (e.g., a distribution resulting from the error of a pipette device used to make the droplets). In some embodiments, the size of the droplets (and thus liquid marble) is homogenous, that is to say substantially all droplets (and thus liquid marbles) have a size that is within a specified error of a median size. In some embodiments, the relative standard error is within 5%, within 2%, within 1% and even within 0.5%.

In some embodiments, such emulsions are made by producing liquid marbles having a metered size, for example, by depositing metered droplets of liquid having a specific selected size (within the error of the depositing device, e.g., pipette) on a surface.

In some embodiments, providing of the plurality of liquid marbles comprises:

making liquid marbles comprising a droplet of the second liquid covered with the shell of the particles;

prior to the immersing of the plurality liquid marbles in the first liquid, selecting only a portion of the made liquid marbles for the immersion;

immersing the selected made liquid marbles in the first liquid; and not immersing the not selected made liquid marbles in the first liquid.

Selecting can be done according to any suitable method. In some embodiments, the selecting is according to a predetermined criteria. In some embodiments, the predetermined criteria is a size of the made liquid marbles, so that:

some sizes of the made liquid marble are selected for the immersion and immersed in the first liquid; and some sizes of the made liquid marbles are not selected for immersion and not immersed in the first liquid. Such selection of liquid marbles is performed using any suitable method, for example by sifting or sieving.

Multiple Distinct Dispersed Phase Populations

As is known to a person having ordinary skill in the art, Pickering emulsions are made by vigorously mixing a mixture of a first liquid, a second liquid and particles so that the composition of the liquid of all of the droplets of the dispersed phase is the same.

Since in the method of making emulsions according to the teachings herein liquid marbles making up the dispersed phase are first provided and only subsequently immersed in the continuous phase, in some embodiments the method is used to make an emulsion having a dispersed phase including at least two distinct populations of liquid marbles, where the two distinct populations differ by having, for example, substantially different size distribution and/or substantially different liquid droplet and/or substantially different particles in the shell of particles covering the droplet. For example, in some embodiments an emulsion according to the teaching herein comprises: a first liquid marble type having a shell of a first type of particle and a second liquid marble type having a shell of a second type of particle.

In some embodiments, a plurality of liquid marbles (e.g., made as described above) is immersed in an already-made emulsion (e.g., a prior art non-Pickering emulsion, or a prior art Pickering emulsion). In such embodiments, the "first liquid" is the continuous phase of the already-made emulsion in which the provided plurality of liquid marbles comprising a droplet of the second liquid are immersed. In other embodiments, at least two different types of liquid marbles are provided (e.g., independently made, substantially as described above) and a plurality of liquid marbles of each of the at least two different types are immersed in the first liquid. In an analogous way, in some embodiments the method is used to make an emulsion having a dispersed phase including substantially any practical desired number of distinct populations, e.g., at least two distinct populations, at least three distinct populations of liquid marbles, at least four distinct populations, at least five distinct populations of liquid marbles and even more, each Thus, in some embodiments, the method further comprises:

d. providing a plurality of liquid marbles intended as a component of the dispersed phase of the emulsion in addition to the plurality of liquid marbles comprising a droplet of the second liquid, each the liquid marble comprising a droplet of a third liquid covered with a shell of particles; and e. subsequent to d, immersing the plurality of liquid marbles comprising a droplet of the third liquid in the first liquid, thereby making the emulsion wherein:

the immersed plurality of liquid marbles comprising a droplet of the second liquid constitutes a portion of the dispersed phase of the emulsion;

the immersed plurality of liquid marbles comprising a droplet of the third liquid constitutes a portion of the dispersed phase of the emulsion; and the first liquid constitutes the continuous phase of the emulsion.

In some embodiments, the third liquid is different from the first liquid. In some embodiments, the third liquid is different from the second liquid. In some embodiments, the third liquid is different is different from both the first and second liquids. In some embodiments, the third liquid is miscible with the first liquid. In some embodiments, the third liquid is miscible with the second liquid. In some embodiments, the third liquid is miscible with both the first and the second liquid. In some embodiments, the third liquid is immiscible with the first liquid. In some embodiments, the third liquid is immiscible with the second liquid. In some embodiments, the third liquid is immiscible with both the first and the second liquid.

In some embodiments, the particles making up the shell of particles covering the droplet of the third liquid are substantially different from the particles making up the shell of particles covering the droplet of the second liquid. Depending on the embodiment, the particles have, for example, a different size distribution and/or a different shape and/or are of a different material or combination of materials.

In some embodiments, the size distribution of the immersed liquid marbles comprising a droplet of the third liquid is different from the size distribution of the immersed liquid marbles comprising a droplet of the second liquid.

Mutually Reactivity of Emulsion Components

In known emulsions, it is not possible to include mutually-reactive components, during the mixing step, such components contact and react.

In contrast, in some embodiments an emulsion according to the teachings herein comprises mutually reactive components, that is to say, components that react (e.g., chemically react) if in contact. Accordingly, in some embodiments, the emulsion comprises at least two components that tend to chemically react when in contact under normal conditions, the at least two components mutually isolated from such contact, by virtue of isolation of at least one of the components in a liquid marble. By normal conditions is meant, for example, standard temperature and pressure, or conditions in which the emulsion is normally stored.

For example, in some embodiments an emulsion comprises at least two different types of liquid marbles: a first liquid marble type including a first component dissolved in the respective droplet of liquid and a second liquid marble type including a second component dissolved in the respective droplet of liquid, where the first component and second component are mutually reactive, that is to say, would react (e.g., chemically react) if the liquid of the droplets of the first and second liquid marble are mixed. In some embodiments, such emulsions are made by forming the two types of liquid marbles separately and subsequently immersing in the same liquid including at least one oil that constitutes the continuous phase.

Embodiments of Particular Emulsions

As is apparent to a person having ordinary skill in the art, the method of making an emulsion according to the teachings herein allow making different types of emulsions, including novel emulsions.

Thus, according to an aspect of some embodiments of the teachings herein, there is also provided an emulsion comprising:
- a continuous phase of a first liquid; and
- a dispersed phase comprising a plurality of liquid marbles, the liquid marbles comprising a droplet of a liquid covered with a shell of particles, wherein the emulsion is characterized by at least one of:
- the first liquid constituting the continuous phase includes a non-soluble constituent suspended therein (e.g., the second liquid is a colloid, an emulsion, water-in-oil emulsion, oil-in-water emulsion, a sol, a hydrocolloid or a suspension);
- a size distribution of the dispersed phase is a non-probability (non-standard) distribution e.g., achieved by selecting made liquid marbles for immersion according to some predetermined criteria, as discussed above;
- the dispersed phase includes at least two distinct populations of liquid marbles, e.g., each population characterized by having different size distribution and/or type of liquid droplet and/or type of particles making up a respective shell, for example made by immersing provided liquid marbles in an already-made prior art emulsion (Pickering or non-Pickering emulsion), or by immersing at least two distinct types of separately-provided liquid marbles;
- the dispersed phase includes at least one distinct population of liquid marbles which droplet of liquid is miscible with the first liquid of the continuous phase;
- the dispersed phase includes at least one distinct population of the liquid marbles which droplet of liquid is substantially different from and miscible with the first liquid of the continuous phase;
- the dispersed phase includes at least one distinct population of liquid marbles which droplet of liquid comprises a non-soluble constituent suspended therein (e.g., a colloid, an emulsion (water-in-oil or oil-in-water), a sol (solid dispersed phase in a liquid continuous phase), a hydrocolloid (hydrophilic polymers in water), a suspension (solid particles dispersed in a liquid continuous phase that do eventually settle);
- the dispersed phase includes at least one distinct population of liquid marbles having an average diameter of not less than 100 micrometers, not less than 200 micrometers, not less than 500 micrometers and even not less than 1 mm;
- the dispersed phase includes at least one distinct population of liquid marbles which shell of particles is a mixture of at least two different materials;
- the dispersed phase includes at least one distinct population of liquid marbles which shell of particles has an average dimension of not less than 10 micrometers, not less than 20 micrometers and even not less than 50 micrometers; and
- the emulsion comprises at least two components that tend to chemically react when in contact under normal conditions, (for example, standard temperature and pressure, or conditions in which the emulsion is normally stored), the at least two components mutually isolated from such contact by virtue of isolation of at least one of the mutually-reactive components in a liquid marble.

EXPERIMENTAL

Second Liquids for Liquid Marbles

Triple distilled water was available in the laboratory of the Inventor. Glycerol (analytical grade) was acquired from Sigma-Aldrich (St. Louis, Mo., USA). Other materials were acquired from Sigma-Aldrich; Fluka (a subsidiary of Sigma-Aldrich); Cabot Corporation (Boston, Mass., USA); Frutarom Industries Ltd. (Haifa, Israel) and Bio-Lab Ltd. (Jerusalem, Israel)

Particles for Marbles

Five types of particles were acquired (Table 1):

TABLE 1

| Type | Source | Particle size (SEM) | Ref | contact angle |
|---|---|---|---|---|
| Hydrophobic | | | | |
| polytetrafluoroethylene (PTFE) | Sigma-Aldrich | 150 nm | 18 | Young 109-112° Apparent 140-160° |
| polyethylene (PE) spectrophotometric grade | Sigma-Aldrich | 130 nm | 37 | Young 96-102° Apparent 130-150° |
| lycopodium powder | Fluka | 30 μm | 38 | Young n/a |

TABLE 1-continued

| Type | Source | Particle size (SEM) | Ref | contact angle |
|---|---|---|---|---|
| Hydrophilic | | | | Apparent 140-155° |
| polyvinylidene fluoride (PVDF) | Sigma-Aldrich | 130 nm | 37 | Young 85-89° Apparent 130-155° |
| carbon black (VulcanXC72R) 95.92% C, 1.05% S, 1.05% O, 0.25% H, and 0.25% N | Cabot | 30 μm | 24 | Young 0° Apparent 100-130° |

Liquid Marble Preparation

Liquid marbles comprising water or glycerol droplets having a shell of the different particles were prepared as taught in Refs 18-24. Specifically, 20 microliter droplets of water were deposited with a micro-dosing pipette onto a superhydrophobic surface, prepared as described in Ref 37. One of five types of particles was then was sprinkled on the superhydrophobic surface and on the droplets resting thereon. Slight tilting of the superhydrophobic surface caused the droplets to roll and to be coated with the particles. In FIG. 1 are depicted water marbles (left side, coated with PVDF, right side with lycopodium powder).

Oils

Twelve oils, all of analytical grade, were acquired, Table 2:

TABLE 2

| Oil | Source | Dipole Moment | Density [kg/m2] | Viscosity [Pa/s (25° C.)] | Solubility in water |
|---|---|---|---|---|---|
| Aromatic | | | | | |
| Toluene | Frutarom | 0.36 D | 0.87 | 0.56 × 10-3 | 0.47 g/L (20° C.) |
| xylene (mixture of o, m, p) | Frutarom | o 0.45 D | 0.88 | 0.812 × 10-3 | o 0.175 g/L (25° C.) |
| | | m | 0.86 | 0.620 × 10-3 | m 0.135 g/L (25° C.) |
| | | p 0.07 D | 0.86 | 0.34 × 10-3 | p 0.198 g/L (25° C.) |
| Halogenated | | | | | |
| carbon tetrachloride | Biolab | 0 | 1.59 | 0.9 × 10-3 | 0.79 g/L (25° C.) |
| dichloromethane | Biolab | 1.60 D | 1.325 | 0.41 × 10-3 | 13 g/L (20° C.) |
| 1,2-dichloroethane | Biolab | 1.80 D | 1.25 | 0.78 × 10-3 | 8.7 g/L (20° C.) |
| Chloroform | Biolab | 1.04 D | 1.48 | 0.54 × 10-3 | 8. g/L (20° C.) |
| silicone oil | | | | | |
| Sylgard 184 (polydimethylsiloxane, PDMS) | Sigma-Aldrich | n/a | 1.03 | 3.9 | insoluble |
| Dow Corning 200 (polydimethylsiloxane, PDMS) | Sigma-Aldrich | n/a | 0.96 | 0.34 | insoluble |
| Polar Oils | | | | | |
| dimethylsulfoxide (DMSO) | Biolab | 3.96 D | 1.1 | 2.0 × 10-3 | miscible |
| N,N,-dimethylformamide (DMF) | Biolab | 3.86 D | 0.96 | 0.8 × 10-3 | miscible |
| Acetone | Biolab | 2.91 D | 0.79 | 0.31 × 10-3 | miscible |
| Ethanol | Biolab | 1.69 D | 0.79 | 1.1 × 10-3 | miscible |

Immersion of Liquid Marbles to Form Water-in-Oil Emulsion

Under ambient conditions, each one of the ten different types of marbles was carefully rolled from the superhydrophobic surface onto the surface of each one of the twelve oils held in a vessel.

The behavior of the liquid marbles was monitored with a rapid camera and a Ramé-Hart Advanced Goniometer Model 500-F1 (Ramé-Hart Instrument Co., Succasunna, N.J., USA).

Silicone Oils

All ten types of marbles sank to the bottom of the vessel containing one of the two silicone oils at a velocity dependent on the viscosity of the oil. All ten types of marbles were stable for an unlimited time (at least one month).

Figure 2A:
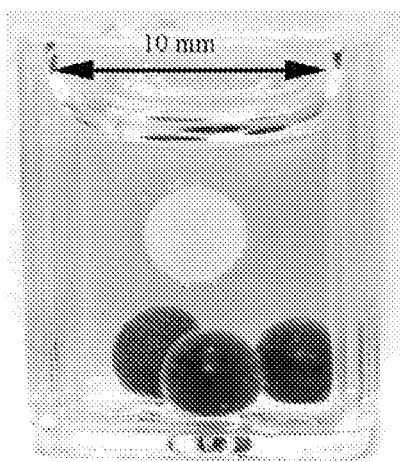
FIG. 2 is a reproduction of a photograph of an emulsion of liquid marbles comprising a droplet of water with a shell of lycopodium powder particles immersed in a polydimethylsiloxane (PDMS) continuous phase.
Figure 2B:
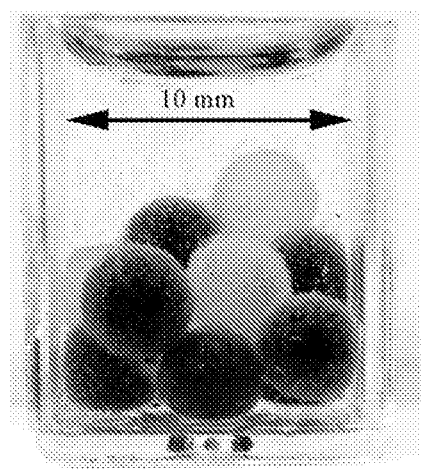

In FIGS. 2A and 2B are depicted water marbles coated with lycopodium powder in a PDMS continuous phase. In FIG. 2A are seen three marbles with 0.01 M KMnO$_4$ resting on the bottom of a vessel containing PDMS with a fourth marble with pure water sinking. In FIG. 2B are seen many marbles resting on the bottom of a vessel containing PDMS, some containing 0.01 M KMnO$_4$ and some pure water.

Aromatic Oils

All ten types of marbles sank to the bottom of the vessel containing an aromatic oil at a velocity dependent on the viscosity of the oil.

Liquid marbles coated with lycopodium particles demonstrated excellent stability and remained stable for an unlimited time (at least 1 month).

Liquid marbles coated with PTFE, PVDF, PE and carbon black particles survived for several minutes. Liquid marbles with any of the four powders burst immediately upon touching the wall of the vessel.

Halogenated Oils

Surprisingly, the liquid marbles did not float on the surface of the halogenated oils. Instead, the liquid marbles settled to just below the surface of the halogenated oils.

Liquid marbles coated with lycopodium particles demonstrated excellent stability and remained stable for an unlimited time (at least 1 month).

Liquid marbles coated with PTFE and PVDF particles survived for 5-10 minutes, and liquid marbles coated with PE survived for approximately a minute. Marbles with any of the three powders burst immediately upon touching the wall of the vessel.

Figure 3:
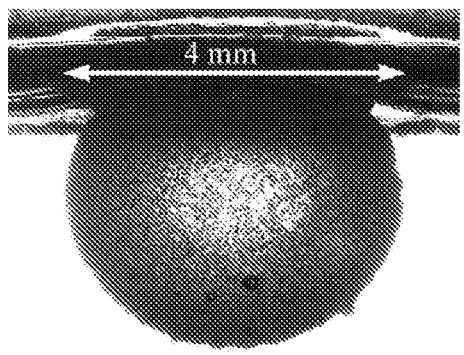
FIG. 3 is a reproduction of a photograph of an emulsion of liquid marbles comprising a droplet of water with a shell of lycopodium powder particles immersed in a 1,2-dichloroethane continuous phase.

In FIG. 3 is depicted a lycopodium powder coated water marble just under the surface of 1,2-dichloroethane.

Polar Oils

Any of the above liquid marbles deposited on the surfaces of acetone, ethanol, DMSO and DMF burst immediately.

The lack of stability of the liquid marbles is attributed to the polarity of the oil.

Determining the Presence of Air Trapped in the Solid Particle Shell

As known in the art, liquid marbles comprise air trapped in the outwardly facing surface of the solid particle shell. As a result, a liquid marble resting on a surface has a very low coefficient friction.

It has been reported [20] that liquid marbles of an NaOH solution floating on a water/alcohol solution including phenolphthalein do not react with the phenolphthalein, attributed to the air in the shell preventing contact therewith.

To determine whether or not air was present on the surface of the liquid marble dispersed phase of an emulsion as described herein, two types of liquid marbles were made as taught therein, a first type comprising a 0.1M NaOH solution with a shell of PVDF particles and the second type comprising a 0.1M NaOH solution with a shell of lycopodium powder particles.

Figure 4:
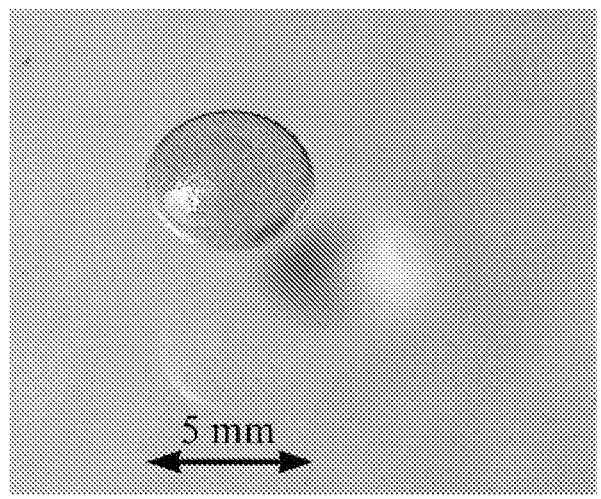
FIG. 4 is a reproduction of a photograph of an emulsion of liquid marbles comprising a droplet of water with a shell of PVDF particles immersed in a $CCl_4$ continuous phase.

A hydrophobic liquid was made by adding 100 microliter of 0.1% phenolphthalein in ethanol to 100 ml of $CCl_4$. The marbles were immersed in the hydrophobic liquid. The red color that developed inside the immersed liquid marbles indicated migration of the phenolphthalein into the liquid marbles and reaction with the NaOH, indicating that there was no layer of air in the shell of the liquid marbles. In FIG. 4, a photograph showing the red color of a liquid marble with a PVDF shell is reproduced.

It is appreciated that certain features of the invention, which are, for clarity, described in the context of separate embodiments, may also be provided in combination in a single embodiment. Conversely, various feature is of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

Citation or identification of any reference in this application shall not be construed as an admission that such reference is available as prior art to the invention.

The priority document of the application, U.S. Provisional Patent Application No. 61/537,799 filed 18 Sep. 2011, incorporated by reference as if fully set-forth herein.

Some aspects of the invention have been published as a scientific article in the Journal of Colloid and Interface Science 2012, 366, pp. 196-199 available online on Sep. 24, 2011, which is included by reference as if fully set-forth herein.

In case of conflict, the specification, including definitions, will take precedence.

REFERENCES (1) Aussillous, P.; Quéré, D. *Nature* 2001, 411, 924-927.
(2) Aussillous, P.; Quéré, D. Properties of liquid marbles, *Proceedings of the Royal Society A* 2006, 46, 973-999.
(3) Mahadevan, L. *Nature* 2001, 411, 895-896.
(4) McHale, G.; Herbertson, D. L.; Elliott, S. J.; Shirtcliffe, N. J.; Newton, M. I. *Langmuir* 2007, 23, 918-924.
(5) Newton, M. I.; Herbertson, D. L.; Elliott, S. J.; Shirtcliffe, N. J.; McHale, G. Electrowetting of liquid marbles, *J. Phys. D: Appl. Phys.* 2007, 40, 20-24.
(6) Bhosale, P. S.; Panchagnula, M. V.; Stretz, H. A., *Appl. Phys. Lett.* 2008, 93, 034109.
(7) Bhosale, P. S.; M. V. Panchagnula, M. V. *Langmuir,* 2010, 26, 10745-10749.
(8) Gao, L.; McCarthy, Th. J. *Langmuir* 2007, 23, 10445-10447.
(9) Dupin, D.; Armes, S. P.; Fujii, S. *J. Am. Chem. Soc.* 2009, 131, 5386-5387.
(10) Fujii, S.; Kameyama, S.; Armes, S. P., Dupin, D.; Suzaki, M.; Nakamura, Y. *Soft Matter* 2010, 6, 635-640.
(11) Dandan, M., Erbil, H. Y. *Langmuir,* 2009; 25: 8362-8367.
(12) Zhao, Y.; Fang, J.; Wang, H.; Wang, X.; Lin, T., *Advanced Materials* 2010, 22, 707-710.
(13) Xue, Yu.; Wang, H.; Zhao, Y.; Dai, L.; Feng, L.; Wang, X.; Lin, T. *Advanced Materials* 2010, 22, 4814-4818.
(14) Eshtiaghi, N.; Liu, J. S.; Shen, W.; Hapgood, K. P. *Powder Technology* 2009, 196, 126-132.
(15) Nguyen, Th. H.; Hapgood, K. P.; Shen, W. *Chemical Engineering Journal* 2010, 162, 396-405.
(16) Tian, J.; Arbatan, T.; Li X.; Shen, W. *Chemical Communications,* 2010, 46, 4734-4736.
(17) Kim, Sh.-H.; Lee, S. Y.; Yang, S. M., *Angew. Chem. Int. Ed.* 2010, 49, 2535-2538.
(18) Bormashenko, E.; Pogreb, R.; Bormashenko, Y.; Musin, A.; Stein, T. *Langmuir* 2008, 24, 12119-12122.
(19) Bormashenko, E.; Pogreb, R.; Whyman, G.; Musin, A.; Bormashenko, Ye.; Barkay, Z. *Langmuir* 2009, 25, 1893-1896.
(20) Bormashenko, E.; Bormashenko, Ye.; Musin, Al.; Barkay, Z. *ChemPhysChem* 2009, 10, 654-656.
(21) Bormashenko, E.; Bormashenko, Y.; Musin, A. *Journal of Colloid and Interface Science* 2009, 333, 419-421.
(22) Bormashenko, E.; Musin, A. *Appl. Surf. Science* 2009, 255, 6429-6431.
(23) Bormashenko, E.; Pogreb, R.; Whyman, G.; Musin, A. *Colloids and Surfaces A* 2009, 351, 78-82.
(24) Bormashenko, E.; Pogreb, R.; Musin, A.; Baiter, R.; Whyman, G.; Aurbach, D. *Powder Technology* 2010, 203, 529-533.
(25) Bormashenko, E.; Bormashenko, Ye.; Pogreb, R.; Gendelman, O. *Langmuir,* 2011, 27, 7-10.
(26) McEleney, P.; Walker, G. M;, Larmour, I. A.; Bell, S. E. J., *Chemical Engineering Journal* 2009, 147, 373-382.
(27) Matsukuma, D.; Watanabe, H.; Yamaguchi, H.; Takahara, A. *Langmuir,* 2011, 27, 1269-1274.
(28) Forny, L.; Pezron, I.; Saleh, Kh.; Guigon, P.; Komunjer, L.; *Powder Technology,* 2007, 171, 15-24.
(32) McHale, G.; Newton, M. I. *Soft Matter,* 2011, 7, 5473-5481

(33) Bormashenko, E.; Bormashenko Ye.; Gendelman, O. *Langmuir* 2010, 26, 12479-12482.
(34) Bormashenko, E.; Baiter, R.; Aurbach, D. *Applied Physics Letters*, 2010, 97, 091908.
(35) Tosun, A.; Erbil, H. Y. *Applied Surface Sci.*, 2009, 256, 1278-1283.
(36) Pickering, S. U. *J. Chem. Soc., Trans.*, 1907, 91, 2001-2021.
(37) Bormashenko, Ed.; Stein, T.; Whyman, G.; Bormashenko, Ye.; Pogreb, R. *Langmuir* 2006, 22, 9982-9985.
(38) Bormashenko, E.; Stein, T.; Pogreb, R.; Aurbach, D. *J. Phys. Chem. C* 2009, 113, 5568-5572.
(39) Antonucci, P. L.; Pino, L; Giordano, N.; Pinna, G. *Mater. Chem. Phys.* 1989, 21, 495-506.
(40) Bormashenko E. Current Opinion in Colloid & Interface Science 16 (2011) 266-271.

The invention claimed is:

1. A method of making an emulsion having a dispersed phase in a continuous phase, the method comprising:
    a. providing a first liquid intended as the continuous phase of the emulsion;
    b. providing a plurality of liquid marbles intended as components of the dispersed phase of the emulsion, said liquid marbles comprising a droplet of a second liquid covered with a shell of particles, wherein said second liquid includes a non-soluble constituent suspended therein, said plurality of liquid marbles comprising one or more type of liquid marble, wherein said providing said plurality of liquid marbles comprises making said liquid marbles by
        placing said particles on a surface;
        setting said particles on a surface;
        allowing said set droplets to roll on said surface so as to be covered by said particles to form said shell of particles, thereby providing said liquid marbles;
    c. subsequent to b, immersing said plurality of liquid marbles in said first liquid,
thereby making the emulsion wherein said immersed plurality of liquid marbles comprising a droplet of said second liquid constitute at least a portion of the dispersed phase of the emulsion and said first liquid constitutes the continuous phase of the emulsion,
wherein said first liquid and said second liquid are mutually immiscible, said first liquid being immiscible in water and said second liquid being miscible in water, so that the emulsion is a water-in-oil emulsion.

2. The method of claim 1, wherein said second liquid is selected from the group consisting of a colloid, an emulsion, oil-in-water emulsion, a sol, a hydrocolloid and a suspension.

3. A method of making an emulsion having a dispersed phase in a continuous phase, the method comprising:
    a. providing a first liquid intended as the continuous phase of the emulsion;
    b. providing a plurality of liquid marbles intended as components of the dispersed phase of the emulsion, said liquid marbles comprising a droplet of a second liquid covered with a shell of particles, said plurality of liquid marbles comprising one or more type of liquid marble, wherein said providing said plurality of liquid marbles comprises making said liquid marbles by
        placing said particles on a surface;
        setting droplets of said second liquid on said surface; and
        allowing said set droplets to roll on said surface so as to be covered by said particles to form said shell of particles, thereby providing said liquid marbles;
    c. subsequent to b, immersing said plurality of liquid marbles in said first liquid,
thereby making the emulsion wherein said immersed plurality of liquid marbles comprising a droplet of said second liquid constitute at least a portion of the dispersed phase of the emulsion and said first liquid constitutes the continuous phase of the emulsion,
wherein said first liquid and said second liquid are mutually immiscible, said first liquid being immiscible in water and said second liquid being miscible in water, so that the emulsion is a water-in-oil emulsion, and
wherein said particles of a shell of a given individual marble are a mixture of at least two different types of particles, each of said different types of particles being composed of different materials.

4. A method of making an emulsion having a dispersed phase in a continuous phase, the method comprising:
    a. providing a first liquid intended as the continuous phase of the emulsion;
    b. providing a plurality of liquid marbles intended as components of the dispersed phase of the emulsion, said liquid marbles comprising a droplet of a second liquid covered with a shell of particles, said plurality of liquid marbles comprising one or more type of liquid marble, wherein said providing said plurality of liquid marbles comprises making said liquid marbles by
        placing said particles on a surface;
        setting droplets of said second liquid on said surface; and
        allowing said set droplets to roll on said surface so as to be covered by said particles to form said shell of particles, thereby providing said liquid marbles;
    c. subsequent to b, immersing said plurality of liquid marbles in said first liquid,
thereby making the emulsion wherein said immersed plurality of liquid marbles comprising a droplet of said second liquid constitute at least a portion of the dispersed phase of the emulsion and said first liquid constitutes the continuous phase of the emulsion,
wherein said first liquid and said second liquid are mutually immiscible, said first liquid being immiscible in water and said second liquid being miscible in water, so that the emulsion is a water-in-oil emulsion, and
wherein said providing of said plurality of liquid marbles comprises:
    making liquid marbles comprising a droplet of said second liquid covered with said shell of said particles;
    prior to said immersing of said plurality liquid marbles in said first liquid, selecting only a portion of said made liquid marbles for said immersion;
    immersing the selected said made liquid marbles in said first liquid; and
    not immersing the not-selected said made liquid marbles in said first liquid.

5. The method of claim 4, wherein said selecting is according to a predetermined size distribution, so that:
    some sizes of said made liquid marble are selected for said immersion and immersed in said first liquid; and
    some sizes of said made liquid marbles are not selected for immersion and not immersed in said first liquid.

6. A method of making an emulsion having a dispersed phase in a continuous phase, the method comprising:
    a. providing a first liquid intended as the continuous phase of the emulsion;
    b. providing a plurality of liquid marbles intended as components of the dispersed phase of the emulsion, said liquid marbles comprising a droplet of a second liquid covered with a shell of particles, said plurality of liquid marbles comprising one or more type of liquid marble, wherein said providing said plurality of liquid marbles comprises making said liquid marbles by
placing said particles on a surface;
setting droplets of said second liquid on said surface; and
allowing said set droplets to roll on said surface so as to be covered by said panicles to form said shell of particles, thereby providing said liquid marbles;
c. subsequent to b, immersing said plurality of liquid marbles in said first liquid;
d. providing an additional plurality of liquid marbles intended as a component of the dispersed phase of the emulsion in addition to the plurality of liquid marbles comprising a droplet of said second liquid, each liquid marble in said additional plurality of liquid marbles comprising a droplet of a third liquid covered with a shell of particles; and
e. subsequent to d, immersing said additional plurality of liquid marbles comprising a droplet of said third liquid in said first liquid,
thereby making the emulsion wherein:
said immersed plurality of liquid marbles comprising a droplet of said second liquid constitutes a portion of the dispersed phase of the emulsion;
said immersed additional plurality of liquid marbles comprising a droplet of said third liquid constitutes a portion of the dispersed phase of the emulsion; and
said first liquid constitutes the continuous phase of the emulsion; and
wherein said first liquid and said second liquid are mutually immiscible, said first liquid being immiscible in water and said second liquid being miscible in water, so that the emulsion is a water-in-oil emulsion.

7. The method of claim 6, wherein said third liquid is different from said first liquid.

8. The method of claim 6, wherein said third liquid is different from said second liquid.

9. The method of claim 6, wherein said particles making up said shell of particles covering said droplet of said third liquid are substantially different from said particles making up said shell of particles covering said droplet of said second liquid.

10. The method of claim 6, wherein the size distribution of said immersed liquid marbles comprising a droplet of said third liquid is different from the size distribution of said immersed liquid marbles comprising a droplet of said second liquid.

* * * * *